United States Patent [19]

Kimura et al.

[11] Patent Number: 5,686,440
[45] Date of Patent: Nov. 11, 1997

[54] AQUEOUS 6-[3-(3,4-DIMETHOXYBENZYL)-AMINO-2-HYDROXYPROPOXY] CARBOSTYRIL COMPOSITION

[75] Inventors: Yuzo Kimura, Tokushima; Shinichi Ishikawa; Yoshito Masuda, both of Itano-gun, all of Japan

[73] Assignee: Otsuka Pharmaceutical Company, Limited, Tokyo, Japan

[21] Appl. No.: 407,027

[22] PCT Filed: Jul. 25, 1994

[86] PCT No.: PCT/JP94/01222

§ 371 Date: Mar. 28, 1995

§ 102(e) Date: Mar. 28, 1995

[87] PCT Pub. No.: WO95/03802

PCT Pub. Date: Feb. 9, 1995

[30] Foreign Application Priority Data

Jul. 28, 1993 [JP] Japan ................................. 5-185973

[51] Int. Cl.⁶ ........................... A61K 31/47; A61K 47/12
[52] U.S. Cl. ...................... 514/187; 514/312; 514/557; 546/141
[58] Field of Search ............................ 514/187, 312, 514/557; 546/141

[56] References Cited

FOREIGN PATENT DOCUMENTS 0355583   2/1990   European Pat. Off. .

*Primary Examiner*—Nathan M. Nutter
*Attorney, Agent, or Firm*—Sughrue,Mion,Zinn,Macpeak & Seas, PLLC

[57] ABSTRACT

This invention provides an aqueous composition wherein a hardly water-soluble active compound, 6-[3-(3,4-dimethoxybenzyl)amino-2-hydroxypropoxy]carbostyril or a salt thereof is dissolved in water in an effective amount, particularly in an amount sufficient for exhibiting the pharmacological activities, by using as a solubilizer DL-lactic acid.

8 Claims, No Drawings

AQUEOUS 6-[3-(3,4-DIMETHOXYBENZYL)-AMINO-2-HYDROXYPROPOXY] CARBOSTYRIL COMPOSITION

TECHNICAL FIELD

This invention relates to an aqueous composition containing a weakly basic compound which is hardly soluble in water and is useful as a medicament, etc. More particularly, it relates to an aqueous composition comprising as an active ingredient 6-[3-(3,4-dimethoxybenzyl)amino-2-hydroxypropoxy]carbostyril or a salt thereof and as a solubilizer DL-lactic acid.

BACKGROUND ART

It is known that the 6-[3-(3,4-dimethoxybenzyl) amino-2-hydroxypropoxy]carbostyril or a salt thereof used as an active ingredient in this invention has positive inotropic activity and is useful as a myocardial contract increasing agent, specifically cardiotonics for the treatment of heart diseases such as congestive heart failure, etc. (cf. U.S. Pat. No. 5,053,514 issued on Oct. 1, 1991), and further that they are also useful as an antihistamines (cf. JP-56-008319) and as an agent for the treatment of thrombosis and a phosphodiesterase inhibitor in view of the excellent platelet aggregation inhibitory activity, phosphodiesterase inhibitory activity, cerebral blood flow increasing activity and platelet aggregate dissociation activity (cf. EP 0 531 548 A1 published on Mar. 17, 1993).

The above active compound is a weakly basic compound which is hardly soluble in water, and hence, it is difficult to prepare an aqueous composition containing said compound. In order to dissolve such a weakly basic compound in water, it is usually dissociated and dissolved by keeping the aqueous mixture at an acidic pH range by incorporating an acidic compound into the aqueous mixture.

For example, it is disclosed in JP-55-031028 (published on Mar. 5, 1980) that a parenteral injection composition containing 1-[1-{3-(4-fluorobenzoyl)propyl}-4-piperidyl]-2,3-dihydrobenzimidazole-2-thion useful as a drug for treating psychosis and neuropathy is prepared by using lactic acid-sodium lactate buffer solution. In this patent, it is also disclosed that when buffer solutions containing other organic acids such as acetic acid, tartaric acid, citric acid, etc. are used, the active compound precipitates, but when lactate buffer is used, no precipitate appears.

Klaus Grohe et al. U.S. Pat. No. 4,705,789 (issued on Nov. 10, 1987) disclose readily-to-use injection and/or infusion solutions of lactic acid salts of piperazinyl-quinolone- and piperazinyl-azaquinolone-carboxylic acids, wherein it is mentioned that the solutions can be stored if, besides the lactic acid salt of at least one of the active substances and, if appropriate, customary auxiliaries, they additionally contain at least one acid which does not lead to precipitates, in particular lactic acid. However, the lactic acid is not specified as to its optical activity.

According to the study by the present inventors, the active compound 6-[3-(3,4-dimethoxybenzyl)amino-2-hydroxypropoxy]carbostyril of this invention forms readily a hardly soluble salt with an acidic compound to be incorporated in order to keep at an acidic pH range, and hence, it is difficult to prepare an aqueous solution having a sufficient concentration of the active compound effective for exhibiting the desired pharmacological activities. Thus, it is difficult to formulate an injection or oral administrative preparation containing said active compound, and hence, the dosage form useful as a medicament is very limited.

DISCLOSURE OF THE INVENTION

The present inventors have further intensively studied as to the physical properties and solubility of the active compound and its salts of this invention and have surprisingly found that the active compound and its salts form a salt having less water-solubility with an optically active L-lactic acid and other various acids but do not form such a less water-soluble salt with an optically inactive DL-lactic acid and further that the active compound and its salts show remarkedly improved solubility in water in the coexistence of DL-lactic acid.

An object of the invention is to provide an aqueous composition comprising as an active ingredient an effective amount of 6-[3-(3,4-dimethoxybenzyl)amino-2-hydroxypropoxy]carbostyril or a salt thereof and as a solubilizer DL-lactic acid and optionally conventional additives. Another object of the invention is to provide an aqueous composition containing the active 6-[3-(3,4-dimethoxybenzyl)amino-2-hydroxypropoxy]carbostyril or a pharmaceutically acceptable salt thereof in a sufficient concentration effective as a medicament. These and other objects and advantages of this invention will be apparent from the following description.

BEST MODE FOR CARRYING OUT THE INVENTION

The aqueous composition of this invention comprises the above active compound 6-[3-(3,4-dimethoxybenzyl)amino-2-hydroxypropoxy]carbostyril or a salt thereof and DL-lactic acid in water. The salt of the active compound includes any conventional salt with an acid, preferably with a pharmaceutically acceptable organic or inorganic acid, for example, salts with organic acids (e.g. succinic acid, tartaric acid, methanesulfonic acid, or maleic acid), and salts with inorganic acids (e.g. hydrochloric acid, or sulfuric acid).

The amount of the active 6-[3-(3,4-dimethoxybenzyl) amino-2-hydroxypropoxy]carbostyril or a salt thereof to be contained in the aqueous composition is dependent on the desired utilities. For the purpose of using as a medicament, the aqueous composition shall contain the active compound in an amount sufficient for exhibiting the desired therapeutic effects, usually in the range of about 0.01 to 70% by weight based on the whole weight of the composition. The amount of DL-lactic acid to be incorporated as a solubilizer is not limited to any specific one but is sufficient when the active compound is well dissolved in the desired amount. Usually, DL-lactic acid is used in an amount of about 1 to 2000 parts by weight to 100 parts by weight of the active 6-[3-(3,4-dimethoxybenzyl)amino-2-hydroxypropoxy]carbostyril or a salt thereof, preferably 10 to 200 parts by weight, more preferably 20 to 80 parts by weight, particularly preferably 30 to 60 parts by weight, to 100 parts by weight of the active compound or a salt thereof. When the amount of DL-lactic acid is less than 10 parts by weight to 100 parts by weight of the active compound or a salt thereof, the desired solubilizing effect is not obtained, but on the other hand, when the DL-lactic acid is used in too much amount, the aqueous composition tends to become disadvantageously irritative. The aqueous composition of this invention is usually in a pH range of about 1.0 to 8.0, preferably about 2.0 to 7.0.

The active 6-[3-(3,4-dimethoxybenzyl)amino-2-hydroxypropoxy]carbostyril to be contained in the aqueous composition is the most preferably a free base, but may be a salt thereof, preferably bisuccinate and bitartrate.

The aqueous composition of this invention may optionally be incorporated by conventional additives, such as buffering agents, antioxidants, preservatives, isotonizing agents, pH adjustors, and the like. The buffering agents include, for example, sodium phosphate, sodium hydrogen phosphate, potassium hydrogen phosphate, boric acid, sodium borate, citric acid, sodium citrate, tartaric acid, sodium tartrate, acetic acid, sodium acetate, epsilon-aminocaproic acid, sodium glutamate, and the like. The antioxidants include, for example, sodium sulfite, sodium pyrosulfite, sodium bisulfite, sodium thiosulfite, ascorbic acid, and the like. The preservatives include, for example, chlorobutanol, benzalkonium chloride, benzethonium chloride, phenylmercuric salts, thimerosal, phenethyl alcohol, methylparaben, propylparaben, and the like. The isotonizing agents are preferably nonelectrolytic substances and include, for example, saccharoses such as glucose, sorbitol, mannitol, fructose, xylitol, and dextrose; polyhydric alcohols such as glycerin; and the like, preferably non-reducing sugars such as D-mannitol and D-sorbitol. The pH adjustors include, for example, sodium hydroxide, hydrochloric acid, and the like. The aqueous composition of this invention may also be incorporated with a solubilizing auxiliary together with DL-lactic acid. The solubilizing auxiliary includes, for example, polyoxyethylene glycol ethers (e.g. polyoxyethylene lauryl ether, polyoxyethylene oleyl ether, etc.), polyethylene glycol higher fatty acid esters (e.g. polyethylene glycol monolaurate, polyethylene glycol monooleate, etc.), polyoxyethylene sorbitan monolaurate, polyoxyethylene fatty acid esters, and the like.

The aqueous composition of this invention is preferably used for the preparation of various pharmaceutical preparations, such as injections, eyedrops, preparations for administering via mucous membranes, preparations suitable for oral administration, and the like. For these pharmaceutical preparations, there may optionally be incorporated other conventional pharmaceutically acceptable carriers or diluents, such as stabilizers, thickening agents, semi-solid base, solid base, excipients, disintegrators, flavors, and the like, in addition to the above-mentioned buffering agents, antioxidants, preservatives, isotonizing agents and pH adjustors.

EXAMPLES

The aqueous composition of this invention is illustrated by the following Example and Preparations, but should not be construed to be limited thereto.

Example 1

The active compound of this invention: 6-[3-(3,4-dimethoxybenzyl)amino-2-hydroxypropoxy]carbostyril (100 parts by weight) and DL-lactic acid (30 parts by weight) were dissolved in water, and the solubility of the active compound was determined at 20° C. As a result, the active compound showed a solubility of more than 70 w/v % as shown in the following Table 1. In comparison purpose, the solubilities of the active compound and its various salts without DL-lactic acid are also shown in Table 1.

TABLE 1

| Active compound* + DL-lactic acid | Solubility at 20° C. (w/v%) More than 70 | pH N.D. |
|---|---|---|
| Active compound | 0.012 | 7.6 |
| Hydrochloride of the active compound | 0.26 | 4.6 |

TABLE 1-continued

| Active compound* + DL-lactic acid | Solubility at 20° C. (w/v%) More than 70 | pH N.D. |
|---|---|---|
| Sulfate of the active compound | 0.31 | 5.6 |
| Hydrobromide of the active compound | 0.32 | 5.3 |
| Monocitrate of the active compound | 0.30 | 4.2 |
| Bimalonate of the active compound | 0.34 | 4.4 |
| Bisuccinate of the active compound | 0.84 | 4.9 |
| Succinate of the active compound | 0.16 | 6.1 |
| Maleate of the active compound | 0.19 | 4.5 |
| Bitartrate of the active compound | 0.63 | 3.7 |
| Tartrate of the active compound | 0.27 | 6.7 |
| Methanesulfonate of the active compound | 0.12 | 6.7 |
| Bifumarate of the active compound | 0.15 | 3.7 |
| L-Lactate of the active compound | 0.34 | 6.0 |

*)The active compound = 6-[3-(3,4-dimethoxybenzyl)amino-2-hydroxypropoxy]carbostyril (hereinafter, the same)

Preparation 1

| Components | Amount |
|---|---|
| The active compound | 1.0 g |
| DL-Lactic acid | 0.4 g |
| D-Mannitol | 4.0 g |
| Sodium hydroxide | q.s. |
| Water for injection | q.s. |
| Totally | 100 ml |

The above components are dissolved in the water for injection and filtered with 0.2 μm membrane filter, and then filled in ampoules or vials, which are sealed and sterilized by heating with steam at 121° C. for 20 minutes to give injection preparation.

Preparation 2

| Components | Amount |
|---|---|
| The active compound | 1.0 g |
| DL-Lactic acid | 0.4 g |
| Glycerin | 2.0 g |
| Benzalkonium chloride | 0.01 g |
| Sodium hydroxide | q.s. |
| Sterilized purified water | q.s. |
| Totally | 100 ml |

The above components are dissolved in the sterilized purified water and filtered with 0.2 μm membrane filter, and then filled in a vessel for eyedrop, which is sealed to give eyedrops.

| Preparation 3 | |
| --- | --- |
| Components | Amount |
| The active compound | 1.0 g |
| DL-Lactic acid | 0.1 g |
| Polyethylene glycol 400 | 20.0 g |
| Polyethylene glycol 1540 | 33.0 g |
| Polyethylene glycol 6000 | 37.0 g |
| Purified water | q.s. |
| Totally | 100 g |

The active compound of this invention is dissolved in water containing DL-lactic acid. The solution is added polyethylene glycol bases, and the mixture is stirred well until it becomes homogeneous, and then filled in a container, which is cooled to form a suppository.

| Preparation 4 | |
| --- | --- |
| Components | Amount |
| The active compound | 20.0 g |
| DL-Lactic acid | 6.0 g |
| Simple syrup | 8.0 g |
| Orange essence | 0.1 g |
| Purified water | q.s |
| Totally | 100 ml |

The above components are dissolved to give syrups.

| Preparation 5 | |
| --- | --- |
| Components | Amount |
| The active compound | 2.0 g |
| DL-Lactic acid | 1.2 g |
| D-Mannitol | 3.0 g |
| Sodium hydroxide | q.s. |
| Water for injection | q.s. |
| Totally | 100 ml |

By using the above components, an injection preparation is prepared in the same manner as described in Preparation 1.

| Preparation 6 | |
| --- | --- |
| Components | Amount |
| Succinate of the active compound | 1.0 g |
| DL-Lactic acid | 0.4 g |
| D-Sorbitol | 4.0 |
| Sodium hydroxide | q.s. |
| Water for injection | q.s. |
| Totally | 100 ml |

By using the above components, an injection preparation is prepared in the same manner as described in Preparation 1.

| Preparation 7 | |
| --- | --- |
| Components | Amount |
| The active compound | 0.1 g |
| DL-Lactic acid | 0.03 g |
| Glycerin | 1.5 g |
| Benzalkonium chloride | 0.01 g |
| Sodium dihydrogen phosphate | 0.04 g |
| Disodium monohydrogen phosphate | 0.01 g |
| Sterilized purified water | q.s. |
| Totally | 100 ml |

By using the above components, eyedrops are prepared in the same manner as descrbined in Preparation 7.

We claim:

1. An aqueous pharmaceutical composition which comprises:

(1) as an active ingredient, 6-[3-(3,4-dimethoxybenzyl) amino-2-hydroxypropoxy]carbostyril or a salt thereof, (2) as a solubilizer, DL-lactic acid, and optionally (3) at least one pharmaceutically acceptable additive, wherein the 6-[3-(3,4-dimethoxy-benzyl)amino-2-hydroxypropoxy]carbostyril or a salt thereof is present in an amount of 0.01 to 70% by weight based on the total weight of the composition, and the DL-lactic acid is present in an amount of 1 to 2000 parts by weight per 100 parts by weight of the 6-[3-(3,4-dimethoxybenzyl)-amino-2-hydroxypropoxy]carbostyril or a salt thereof.

2. The aqueous pharmaceutical composition according to claim 1, wherein the amount of the DL-lactic acid is in the range of 10 to 200 parts by weight to 100 parts by weight of the 6-[3-(3,4-dimethoxybenzyl)amino-2-hydroxypropoxy]carbostyril or a salt thereof.

3. The aqueous pharmaceutical composition according to claim 1, wherein the amount of the DL-lactic acid is in the range of 20 to 80 parts by weight to 100 parts by weight of the 6-[3-(3,4-dimethoxybenzyl)amino-2-hydroxypropoxy]carbostyril or a salt thereof.

4. The aqueous pharmaceutical composition according to claim 1, wherein the amount of the DL-lactic acid is in the range of 30 to 60 parts by weight to 100 parts by weight of the 6-[3-(3,4-dimethoxybenzyl)amino-2-hydroxypropoxy]carbostyril or a salt thereof.

5. The aqueous pharmaceutical composition according to claim 4, wherein said composition has a pH value of 2 of 7.

6. The aqueous pharmaceutical composition according to claim 1, wherein the salt is a bisuccinate salt or a bitartrate salt.

7. The aqueous pharmaceutical composition according to claim 1, wherein the pharmaceutically acceptable additive is selected from the group consisting of a buffering agent, an antioxidant, a preservative, an isotonizing agent, and a pH adjustor.

8. The aqueous pharmaceutical composition according to claim 7, wherein the isotonizing agent is D-sorbitol or D-mannitol.

* * * * *